United States Patent
Kellogg et al.

(10) Patent No.: US 7,332,326 B1
(45) Date of Patent: *Feb. 19, 2008

(54) CENTRIPETALLY-MOTIVATED MICROFLUIDICS SYSTEM FOR PERFORMING IN VITRO HYBRIDIZATION AND AMPLIFICATION OF NUCLEIC ACIDS

(75) Inventors: Gregory J. Kellogg, Cambridge, MA (US); Bruce L. Carvalho, Watertown, MA (US); Norman F. Sheppard, Jr., Bedford, MA (US); Kevin E. Noonan, Chicago, IL (US)

(73) Assignee: Tecan Trading AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/570,492

(22) Filed: May 12, 2000

Related U.S. Application Data

(60) Provisional application No. 60/134,086, filed on May 14, 1999.

(51) Int. Cl.
*G01N 9/30* (2006.01)
(52) U.S. Cl. .................. 435/287.2; 435/286.5; 435/288.5; 435/288.7; 422/54; 422/64
(58) Field of Classification Search .................. 422/64; 435/286.5, 287.2, 288.4, 288.5, 288.6, 288.7
See application file for complete search history.

(56) References Cited

U.S. PATENT DOCUMENTS

| | | | |
|---|---|---|---|
| 4,683,195 A | 7/1987 | Mullis et al. .................. 435/6 |
| 4,683,202 A | 7/1987 | Mullis .......................... 435/91 |
| 4,988,617 A | 1/1991 | Landegren et al. ............. 435/6 |
| 5,304,487 A | 4/1994 | Wilding et al. ............. 435/291 |
| 6,030,581 A * | 2/2000 | Virtanen ..................... 422/68.1 |
| 6,063,589 A | 5/2000 | Kellogg et al. ............... 435/24 |
| 6,117,630 A * | 9/2000 | Reber et al. .................... 435/4 |

FOREIGN PATENT DOCUMENTS

| | | |
|---|---|---|
| EP | 0693560 A2 | 1/1996 |
| WO | WO93/22053 | 11/1993 |
| WO | WO93/22058 | 11/1993 |
| WO | WO97/21090 | 12/1997 |
| WO | WO98/54580 | 3/1998 |
| WO | WO98/53311 | 11/1998 |

OTHER PUBLICATIONS

Wilding et al., 1994, Clin. Chem. 40:43-47.
Kopp et al., 1998, Science 280:1046.

* cited by examiner

*Primary Examiner*—David Redding
(74) *Attorney, Agent, or Firm*—Frommer Lawrence & Haug LLP; Thomas J. Kowalski; Deborah L. Lu

(57) ABSTRACT

This invention relates to methods and apparatus for performing microanalytic and microsynthetic analyses and procedures. The invention provides a microsystem platform and a micromanipulation device for manipulating the platform that utilizes the centripetal force resulting from rotation of the platform to motivate fluid movement through microchannels. The microsystem platforms of the invention are provided having arrays of thermal control regions, wherein fluid applied to the platform can be placed at a temperature and maintained at that temperature for a time that is dependent on the path length of the channel in the region, the cross-section dimension of the channel, and the rotational speed of the platform. Methods specific for the apparatus of the invention for performing any of a wide variety of microanalytical or microsynthetic processes are provided.

48 Claims, 7 Drawing Sheets

CENTRIPETALLY-MOTIVATED MICROFLUIDICS SYSTEM FOR PERFORMING IN VITRO HYBRIDIZATION AND AMPLIFICATION OF NUCLEIC ACIDS

This application claims priority to U.S. Provisional application Ser. No. 60/134,086, filed May 14, 1999, the disclosure of which is explicitly incorporated by reference herein.

BACKGROUND OF THE INVENTION

1. Field of the Invention

This invention relates to methods and apparatus for performing microanalytic and microsynthetic analyses and procedures. In particular, the invention relates to microminiaturization of genetic, biochemical and bioanalytic processes. Specifically, the invention relates to performing bioanalytic and biotechnological processes that are dependent on incubating samples and solutions at different temperatures, and particularly reactions that required sequential sample incubation at alternating temperatures, including in vitro amplification reactions and most particularly the polymerase chain reaction. Methods for performing any of a wide variety of such microanalytical or microsynthetic processes using the microsystems apparatus of the invention are also provided.

2. Background of the Related Art

In the biological and biochemical arts, analytical procedures frequently require incubation of biological samples and reaction mixtures at temperatures greater than ambient temperature. Moreover, many bioanalytical and biosynthetic techniques require incubation at more than one temperature, either sequentially or over the course of a reaction scheme or protocol.

One example of such a bioanalytical reaction is the polymerase chain reaction. The polymerase chain reaction (PCR) is a technique that permits amplification and detection of nucleic acid sequences. See U.S. Pat. Nos. 4,683,195 to Mullis et al. and 4,683,202 to Mullis. This technique has a wide variety of biological applications, including for example, DNA sequence analysis, probe generation, cloning of nucleic acid sequences, site-directed mutagenesis, detection of genetic mutations, diagnoses of viral infections, molecular "fingerprinting," and the monitoring of contaminating microorganisms in biological fluids and other sources. The polymerase chain reaction comprises repeated rounds, or cycles, of target denaturation, primer annealing, and polymerase-mediated extension; the reaction process yields an exponential amplification of a specific target sequence.

Methods for miniaturizing and automating PCR are desirable in a wide variety of analytical contexts, particularly under conditions where a large multiplicity of samples must be analyzed simultaneously or when there is a small amount of sample to be analyzed.

In addition to PCR, other in vitro amplification procedures, including ligase chain reaction as disclosed in U.S. Pat. No. 4,988,617 to Landegren and Hood, are known and advantageously used in the prior art. More generally, several important methods known in the biotechnology arts, such as nucleic acid hybridization and sequencing, are dependent upon changing the temperature of solutions containing sample molecules in a controlled fashion. Automation and minimization of the performance of these methods are desirable goals in the art.

Mechanical and automated fluid handling systems and instruments produced to perform automated PCR have been disclosed in the prior art.

U.S. Pat. No. 5,304,487, issued Apr. 19, 1994 to Wilding et al. teach fluid handling on microscale analytical devices.

International Application, Publication No. WO93/22053, published Nov. 11, 1993 to University of Pennsylvania disclose microfabricated detection structures.

International Application, Publication No. WO93/22058, published Nov. 11, 1993 to University of Pennsylvania disclose microfabricated structures for performing polynucleotide amplification.

Wilding et al., 1994, *Clin. Chem.* 40: 43-47 disclose manipulation of fluids on straight channels micromachined into silicon.

Kopp et al., 1998, *Science* 280: 1046 discloses microchips for performing in vitro amplification reactions using alternating regions of different temperature.

One drawback of the synthetic microchips disclosed in the prior art for performing PCR and other temperature-dependent bioanalytic reactions has been the difficulty in designing systems for moving fluids on the microchips through channels and reservoirs having diameter in the 10-100 μm range. This is due in part to the need for high-pressure pumping means for moving fluid through the small sizes of the components of these microchips. These disabilities of the prior art microchips limits the usefulness of these devices for miniaturizing and automating PCR and other bioanalytic processes.

Some of the present inventors have developed a microsystem platform and a micromanipulation device to manipulate said platform by rotation, thereby utilizing the centripetal forces resulting from rotation of the platform to motivate fluid movement through microchannels embedded in the microplatform, as disclosed in co-owned U.S. Pat. No. 6,063,589, issued May 16, 2000, and co-owned and co-pending patent applications U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; and 09/315,114, filed May 19, 1999, the disclosures of each of which are explicitly incorporated by reference herein.

SUMMARY OF THE INVENTION

This invention provides microsystems platforms as disclosed in co-owned U.S. Pat. No. 6,063,589, issued May 16, 2000, and co-owned and co-pending patent applications U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; and 09/315,114, filed may 19, 1999, the disclosures of each of which are explicitly incorporated by reference herein.

The invention provides apparatus and methods for performing microscale processes on a microplatform, whereby fluid is moved on the platform in defined channels motivated by centripetal force arising from rotation of the platform. The first element of the apparatus of the invention is a microplatform that is a rotatable structure, most preferably a disk, the disk comprising fluid (sample) inlet ports, fluidic microchannels, reagent reservoirs, reaction chambers, detection chambers and sample outlet ports, generically termed "microfluidic structures," and most preferably heating elements comprising a portion of the surface area of the platform for heating fluids contained therein to temperatures greater than ambient temperature. The disk is rotated at speeds from about 1-30,000 rpm for generating centripetal acceleration that enables fluid movement through the microfluidic structures of the platform. The disks of the invention also preferably comprise air outlet ports and air displacement channels. The air outlet ports and in particular the air displacement ports provide a means for fluids to displace air, thus ensuring uninhibited movement of fluids on the disk. Specific sites on the disk also preferably comprise elements that allow fluids to be analyzed, as well as detectors for each of these effectors. Alternatively some or all of these elements can be contained on a second disk that is placed in optical or direct physical contact, most preferably thermal contact, with the first platform disk.

The second element of the invention is a micromanipulation device that is a disk play/reader device that controls the function of the disk. This device comprises mechanisms and motors that enable the disk to be loaded and rotated. In addition, the device provides means for a user to operate the microsystems in the disk and access and analyze data, preferably using a keypad and computer display.

The invention specifically provides microsystems platforms comprising regions of the platform surface that comprise or are in thermal contact with heating elements, wherein fluids contained in such regions, most preferably in microchannels as defined herein, are efficiently heated to and maintained at temperatures greater than ambient for a time that is proportional to the length of the longitudinal extent or path of the microchannel in the region, the viscosity of the fluid and inversely proportional to the product of the square of the hydraulic diameter of the microchannel, the square of the rotational speed of the platform, the average distance of the fluid in the channels from the center of the disk and the radial extent of the fluid subject to the centripetal force. For fluids with defined viscosities, one combine the controlled rotational speed of the platform with engineered or designed microchannels to control the flow rate of fluids within the disk.

In certain preferred embodiments, said regions of the platform comprising or in thermal contact with a heating element or multiplicity thereof (termed herein a "thermal array") comprise an array of heating elements that can be operated at different temperatures. In these embodiments, the proportion of time that a fluid contained in said region, most preferably in a microchannel, is maintained at a particular temperature is directly proportional to the longitudinal extent of the microchannel in the region. The path of the microchannel on the surface of the platform in the region comprising or in the thermal contact with a heating element or thermal array thereof as described herein can be straight, curved, spiral, "zig-zag," or meandering, and the path can repeatedly enter and leave any particular temperature region on the disk.

This arrangement of heating elements into thermal arrays and transit of microchannels through such arrays provides for incubating fluid contained in such microchannels at different temperatures without having to use the heating elements to actively change the temperature of the platform. This arrangement permits the establishment of regions of the platform that are maintained at any particular temperature greater than ambient, whereby heating and incubating a fluid is dependent on the length of the portion of the microchannel in that region of the platform, and hence the amount of time the fluid spends in that region as it transits the microchannel under the influence of centripetal force from rotation of the platform.

One embodiment of such a thermal array comprises a region of the platform comprising or in thermal contact with a single heating element. In these embodiments, the temperature of fluids contained in such regions, most preferably in microchannels, is alternated by movement of the fluid in the microchannel between an elevated temperature from operation of the heating element and the ambient temperature of the platform by traversal through a microchannel that enters and leaves the area comprising or in thermal contact with the heating element. The proportion of the time that the fluid is maintained at the elevated temperature is directly proportional to the extent of the longitudinal path of the microchannel in the region comprising or in the thermal contact with the heating element. Heating elements on the platforms of the invention encompassed by this aspect can produce elevated temperatures from 37° C. to about 95° C., and the absolute amount of time the fluid is kept at the elevated temperature can be varied with platform rotational speed. The relative amount of time that the fluid is maintained at the elevated temperature is dependent on the geometry of the microchannel path on the platform, the average distance of the fluid in the channels from the center of the disk, the radial extent of the fluid subject to the centripetal force and the rotation rate of the platform and can be made invariant for any particular geometry in any particular embodiment of the platforms of this aspect of the invention by the judicious combination of these variables.

Another embodiment of such an thermal array comprises a region of the platform comprising or in thermal contact with two heating elements, which will be understood to encompass embodiments having a single heating element in thermal contact with two discrete regions of the platform. In one aspect of these embodiments of the invention, the areas of the platform in contact with each of the two heating elements are immediately adjacent to one another. In these embodiments, the two different areas can be operated at two different temperatures greater than the ambient temperature of the platform. In these embodiments, the temperature of fluids contained in such regions, most preferably in microchannels, is alternated between each of the two elevated temperatures produced by operation of the heating elements by traversal through a microchannel that enters and leaves the each area comprising or in thermal contact with each of the heating elements. The proportion of the time that the fluid is maintained at each of the elevated temperatures is directly proportional to the extent of the longitudinal path of the microchannel in the region comprising or in thermal contact with each of the heating elements. Platforms of the invention encompassed by this aspect can be used wherein each of the areas is independently maintained at elevated temperatures from 37° C. to about 95° C. by the heating elements, and the amount absolute amount of time the fluid is kept at each of the elevated temperature can be varied with platform rotational speed. The relative amount of time that the fluid is maintained at each of the elevated temperature is dependent on the geometry of the microchannel path on the platform, the average distance of the fluid in the channels from the center of the disk, the radial extent of the fluid subject to the centripetal force and the rotation rate of the platform and can be made invariant for any particular geometry in any particular embodiment of the platforms of this aspect of the invention by the judicious combination of these variables.

In related embodiments, the thermal array comprises an areas of the platform comprising or in thermal contact with more than two, most preferably three, heating elements, wherein the temperatures of each of these areas can be independently maintained at a different temperature greater than the ambient temperature of the platform. In preferred embodiments, each of the areas of the platform in contact with each of the heating elements are immediately adjacent to one another. In these embodiments, the three different areas can be operated at three different temperatures greater than the ambient temperature of the platform. In these embodiments, the temperature of fluids contained in such regions, most preferably in microchannels, is alternated between each of the elevated temperatures from operation of the heating elements by traversal through a microchannel that enters and leaves each area comprising or in thermal contact with each of the heating elements. The proportion of the time that the fluid is maintained at each of the elevated temperatures is directly proportional to the extent of the longitudinal path of the microchannel in the region comprising or in thermal contact with each of the heating elements. Platforms of the invention encompassed by this aspect can be used wherein each of the areas is independently maintained at elevated temperatures from 37° C. to about 95° C., and the absolute amount of time the fluid is kept at each of the elevated temperature can be varied with platform rotational speed. The relative amount of time that the fluid is maintained at each of the elevated temperature is dependent on the geometry of the microchannel path on the platform, the average distance of the fluid in the channels from the center of the disk, the radial extent of the fluid subject to the centripetal force and the rotation rate of the platform and can be made invariant for any particular geometry in any particular embodiment of the platforms of this aspect of the invention by the judicious combination of these variables.

In an alternative embodiment, the thermal array comprises two or more areas of the platform surface comprising or in thermal contact with a heating element, wherein at least one of said areas is separated from another areas by an area that does not comprise and is not in thermal contact with a heating element. This intervening areas of the array is maintained at the ambient temperature of the platform. In these embodiments, a microchannel is constructed in the thermal array to traverse both the areas comprising or in thermal contact with the heating elements, and the area or areas that do not comprise or are not in thermal contact with a heating element. The proportion of time that fluid contained in such microchannels is at an elevated temperature or ambient temperature is directly proportional to the extent of the longitudinal path of the microchannel in the areas that do or do not comprise or are or are not in thermal contact with each of the heating elements.

In preferred embodiments, heat originates from a single face of the platform, most preferably from a position underneath the microfluidics components. In alternative embodiments, a fluidic disk or manifold is positioned between two thermal regulation layers each comprising heating elements to provide heating on both surfaces of the microfluidic disk.

In further alternative embodiments, the microsystems platforms of the invention comprise a multiplicity of the same or different embodiments of the thermal arrays described herein. Most preferably, each of the microchannels traversing said arrays is in fluid contact with one or a multiplicity of sample input ports or fluid holding chambers comprising a biological sample or reaction mixture. In additional preferred embodiments, each microchannel is also fluidly connected with a collection chamber, most preferably wherein each microchannel is uniquely in fluid contact with a particular collection chamber.

In preferred embodiments, the thermal arrays and regions of elevated temperatures constructed in the surface of the platforms of the invention comprise a thermal heating element. In preferred embodiments, the thermal heating element is a resistive heater element.

The invention also provides methods for using the microsystems platform for performing any bioanalytical or biosynthetic reaction that requires or advantageously includes the step of incubating a biological sample or reaction mixture at one or a multiplicity of temperatures greater than ambient temperature, and more preferably wherein incubation of the biological sample or reaction mixture at one or a multiplicity of temperatures greater than ambient temperature is performed sequentially or repetitively or both. In a preferred embodiment, the bioanalytical or biosynthetic reaction is nucleic acid hybridization, polymerase chain reaction or ligase chain reaction.

Certain preferred embodiments of the apparatus of the invention are described in greater detail in the following sections of this application and in the drawings.

DETAILED DESCRIPTION OF PREFERRED EMBODIMENTS

Figure 1:
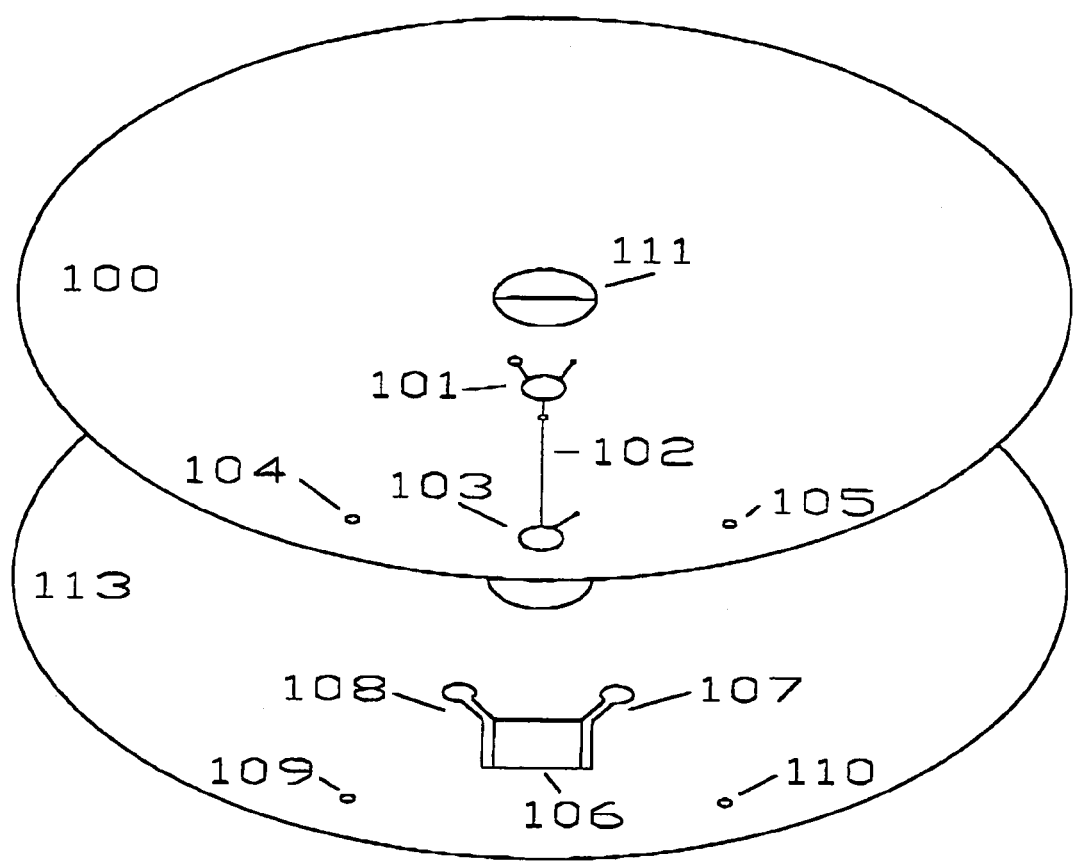
FIG. 1 depicts an oblique view of a microsystems platform of the invention.

This invention provides a microplatform and a micromanipulation device as disclosed in co-owned U.S. Pat. No. 6,063,589, issued May 16, 2000, and co-owned and co-pending patent applications U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; 09/315,114, filed May 19, 1999, the disclosures of each of which are explicitly incorporated by reference herein, adapted for performing microanalytical and microsynthetic assays of biological samples.

For the purposes of this invention, the term "sample" will be understood to encompass any fluid, solution or mixture, either isolated or detected as a constituent of a more complex mixture, or synthesized from precursor species. In particular, the term "sample" will be understood to encompass any biological species of interest, and preferably nucleic acid, and most preferably a nucleic acid in a solution wherein detection or amplification of said nucleic acid is accomplished. The term "biological sample" or "biological fluid sample" will be understood to mean any biologically-derived analytical sample, including but not limited to blood, plasma, serum, lymph, saliva, tears, cerebrospinal fluid, urine, sweat, plant and vegetative extracts, semen, and ascites fluid.

For the purposes of this invention, the term "a centripetally motivated fluid micromanipulation apparatus" is intended to include analytical centrifuges and rotors, microscale centrifugal separation apparatuses, and most particularly the microsystems platforms and disk handling apparatuses as described in co-owned U.S. Pat. No. 6,063,589, issued May 16, 2000, and co-owned and co-pending patent application U.S. Ser. Nos. 08/761,063, filed Dec. 5, 1996;

08/768,990, filed Dec. 18, 1996; 08/910,726, filed Aug. 12, 1997; 08/995,056, filed Dec. 19, 1997; 09/315,114, filed May 19, 1999, the disclosures of each of which are explicitly incorporated by reference herein.

For the purposes of this invention, the term "microsystems platform" is intended to include centripetally-motivated microfluidics arrays as described in co-owned U.S. Pat. No. 6,063,589, issued May 16, 2000, and co-owned and co-pending patent applications U.S. Ser. Nos. 08/761,063, filed Dec. 5, 1996; 08.768,990, filed Dec. 18, 1996; 08/910,726, filed Aug. 12, 1997; 08/995,056, filed Dec. 19, 1997; 09/315,114, filed May 19, 1999, the disclosures of each of which are explicitly incorporated by reference herein.

For the purposes of this invention, the terms "capillary", "microcapillary" and "microchannel" will be understood to be interchangeable and to be constructed of either wetting or non-wetting materials where appropriate.

For the purposes of this invention, the term "fluid chamber," "fluid holding chamber" and "collection chamber" will be understood to mean a defined volume on a microsystems platform of the invention comprising a fluid.

For the purposes of this invention, the terms "entry port" and "fluid input port" will be understood to mean a defined volume on a microsystems platform of the invention comprising a means for applying a fluid to the platform.

For the purposes of this invention, the terms "exit port" and "fluid outlet port" will be understood to mean a defined volume on a microsystems platform of the invention comprising a means for removing a fluid from the platform.

For the purposes of this invention, the term "capillary junction" will be understood to mean a junction of two components wherein one or both of the lateral dimensions of the junction are larger than the corresponding dimensions the capillary. In wetting or wettable systems, such junctions are where capillary valving occurs, because fluid flow through the capillaries is stopped at such junctions. In non-wetting or non-wettable junctions, the exit from the chamber or reservoir is where the capillary junction occurs. In general, it will be understood that capillary junctions are formed when the dimensions of the components change from a small diameter (such as a capillary) to a larger diameter (such as a chamber) in wetting systems, in contrast to non-wettable systems, where capillary junctions form when the dimensions of the components change from a large diameter (such as a chamber) to a small diameter (such as a capillary).

For the purposes of this invention, the term "capillary action" will be understood to mean fluid flow in the absence of rotational motion or centripetal force applied to a fluid on a rotor or platform of the invention.

For the purposes of this invention, the term "capillary microvalve" will be understood to mean a capillary microchannel comprising a capillary junction whereby fluid flow is impeded and can be motivated by the application of pressure on a fluid, typically by centripetal force created by rotation of the rotor or platform of the invention.

For the purposes of this invention, the term "sacrificial valve" will be understood to mean a valve preferably made of a fungible material that can be removed from the fluid flow path. In preferred embodiments, said sacrifical valves are wax valves and are removed from the fluid flow path by heating, using any of a variety of heating means including infrared illumination and most preferably by activation of heating elements on or embedded in the platform surface as described in co-owned U.S. Pat. No. 6,063,589, incorporated by reference.

For the purposes of this invention, the term "in fluid communication" or "fluidly connected" is intended to define components that are operably interconnected to allow fluid flow between components. In preferred embodiments, the platform comprises a rotatable platform, more preferably a disk, whereby fluid movement on the disk is motivated by centripetal force upon rotation of the disk.

For the purposes of this invention, the term "air displacement channels" will be understood to include ports in the surface of the platform that are contiguous with the components (such as microchannels, chambers and reservoirs) on the platform, and that comprise vents and microchannels that permit displacement of air from components of the platforms and rotors by fluid movement.

The microplatforms of the invention (preferably and hereinafter collectively referred to as "disks"; for the purposes of this invention, the terms "microplatform", "microsystems platform" and "disk" are considered to be interchangeable), are provided to comprise one or a multiplicity of microsynthetic or microanalytic systems. Such microsynthetic or microanalytic systems in turn comprise combinations of related components as described in further detail herein that are operably interconnected to allow fluid flow between components upon rotation of the disk. These components can be microfabricated as described below either integral to the disk or as modules attached to, placed upon, in contact with or embedded in the disk. For the purposes of this invention, the term "microfabricated" refers to processes that allow production of these structures on the sub-millimeter scale. These processes include but are not restricted to molding, photolithography, etching, stamping and other means that are familiar to those skilled in the art.

The invention also comprises a micromanipulation device for manipulating the disks of the invention, wherein the disk is rotated within the device to provide centripetal force to effect fluid flow on the disk. Accordingly, the device provides means for rotating the disk at a controlled rotational velocity, for stopping and starting disk rotation, and advantageously for changing the direction of rotation of the disk. Both electromechanical means and control means, as further described herein, are provided as components of the devices of the invention. User interface means (such as a keypad and a display) are also provided, as further described in co-owned U.S. Pat. No. 6,063,589, issued May 16, 2000, and co-owned and co-pending patent applications U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; 09/315,114, filed May 19, 1999, the disclosures of each of which are explicitly incorporated by reference herein.

The invention provides a combination of specifically-adapted microplatforms that are rotatable, analytic/synthetic microvolume assay platforms (collectively referred to herein as a "disk" or "disc"), and a micromanipulation device for manipulating the platform to achieve fluid movement on the platform arising from centripetal force on the platform as result of rotation. The platform of the invention is preferably and advantageously a circular disk; however, any platform capable of being rotated to impart centripetal for a fluid on the platform is intended to fall within the scope of the invention. Preferably, the disk incorporates microfabricated mechanical, optical, and fluidic control components on platforms made from, for example, plastic, silica, quartz, metal or ceramic. These structures are constructed on a sub-millimeter scale by molding, photolithography, etching, stamping or other appropriate means.

Platforms of the invention such as disks and the components comprising such platforms are advantageously provided having a variety of composition and surface coatings appropriate for a particular application. Platform composition will be a function of structural requirements, manufacturing processes, and reagent compatibility/chemical resistance properties. Specifically, platforms are provided that are made from inorganic crystalline or amorphous materials, e.g., silicon, silica, quartz, inert metals, or from organic materials such as plastics, for example, poly(methyl methacrylate) (PMMA), acetonitrile-butadiene-styrene (ABS), polycarbonate, polyethylene, polystyrene, polyolefins, polypropylene and metallocene. These may be used with unmodified or modified surfaces as described below. Also provided by the invention are platforms made of composites or combinations of these materials, for example, platforms manufactures of a plastic material having embedded therein an optically transparent glass surface comprising for example the detection chamber of the platform. The surface properties of these materials may be modified for specific applications, as disclosed in co-owned U.S. Pat. No. 6,063,589, issued May 16, 2000, and co-owned and co-pending patent application U.S. Ser. Nos. 08/761,063, filed Dec. 5, 1996; 08/768,990, filed Dec. 18, 1996; 08/910,726, filed Aug. 12, 1997; 08/95,056, filed Dec. 19, 1997; 09/315,114, filed May 19, 1999, the disclosures of each of which are explicitly incorporated by reference herein.

The platforms of the invention can be used to perform any microanalytical and microsynthetic reaction requiring that the sample be incubated at one or a multiplicity of temperatures greater than the ambient temperature of the disk for a controlled amount of time. Most Preferably, the microsystems platforms of the invention are adapted for performing nucleic acid hybridization assays and in vitro amplification reactions, such as the polymerase chain reaction or ligase chain reaction, using centrifugal action to move a fluid reaction mixture between various temperature controlled regions on a microfluidics disc.

For performing the polymerase chain reaction in conventional thermal cyclers, the reaction mixture remains at one location and the temperature of this location is typically cycled between a denaturation temperature (>90° C.), an annealing temperature (which varies with the sequence complexity, length and hybridization fidelity of the oligonucleotide primers) and an extension temperature (usually around 70° C. for reactions performed with Taq polymerase). Typical thermal cyclers are able to heat and cool at rates between 1° C./sec and 2° C./sec, with a temperature accuracy and precision of approximately +/− 1° C.

In contrast, the microsystem platforms of the invention do not require active temperature changes of any particular region of the platform such as a reaction chamber. Rather, thermal arrays comprising adjacent regions of different temperature are provide by the platforms of the invention, so that temperature changes are effected by transit of a fluid through a microchannel from one temperature region to another region at a different temperature. The amount of time a fluid is maintained at a particular temperature is determined by the transit time of the fluid through any particular region of a thermal array at a particular temperature, which is proportional to the longitudinal extent or length of the microchannel in that temperature region.

The present invention provides components of the microsystems platform that can perform at levels sufficiently equivalent to these specifications as to enable microminiaturization of in vitro amplification reactions on such platforms.

Fluid (including reagents, samples and other liquid components) movement is controlled by centripetal acceleration due to rotation of the platform. The magnitude of centripetal acceleration required for fluid to flow at a rate and under a pressure appropriate for a particular microsystem is determined by factors including but not limited to the effective radius of the platform, the interior diameter of microchannels, the position angle of the microchannels on the platform with respect to the direction of rotation, and the speed of rotation of the platform. In certain embodiments of the methods of the invention a metered amount of the fluid sample applied to the platform is transferred from a fluid holding chamber to a microchannel as described in co-owned U.S. Pat. No. 6,063,589, issued May 16, 2000, and co-owned and co-pending patent applications U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; 09/315,114, filed May 19, 1999, the disclosures of each of which are explicitly incorporated by reference herein. In preferred embodiments, the metered amount of the fluid sample provided on an inventive platform is from about 10 µL to about 500 µL.

The components of the platforms of the invention are in fluidic contrast with one another. In preferred embodiments, fluidic contact is provided by microchannels comprising the surface of the platforms of the invention. Microchannel sizes are optimally determined by specific applications and by the amount of delivery rates required for each particular embodiment of the platforms and methods of the invention. Microchannel sizes can range from 0.1 µm to a value close to the thickness of the disk (e.g., 1 mm). In preferred embodiments, the interior dimension of the microchannel is from 1 to about 200 µm, more preferably about 50 µm for microchannels having a circular aspect and 50 µm×50 µm for microchannels having a square aspect. Microchannel and reservoir shapes can be trapezoid, circular or other geometric shapes as required. Microchannels preferably are embedded in a microsystem platform having a thickness of about 0.1 to 100 mm, wherein the cross-sectional dimension of the the microchannels across the thickness dimension of the platform is less than 500 µm and can be from 1 to 90 percent of said cross-sectional dimension of the platform. Reagent reservoirs, reaction chambers, detections chambers and sample inlet and outlet ports preferably are embedded in a microsystem platform having a thickness of about 0.1 to 100 mm, wherein the cross-sectional dimension of the microchannels across the thickness dimension of the platform is from 1 to 75 percent of said cross-sectional dimension of the platform. In preferred embodiments, delivery of fluids through such channels is achieved by the coincident rotation of the platform for a time and at a rotational velocity sufficient to motivate fluid movement between the desired components.

The flow rate through a channel is inversely proportional to the length of the longitudinal extent or path of the microchannel in the region and the viscosity of the fluid and proportional to the product of the square of the hydraulic diameter of the microchannel, the square of the rotational speed of the platform, the average distance of the fluid in the channels from the center of the disk and the radial extent of the fluid subject to the centripetal force. Since the hydraulic diameter of a channel is proportional to the ratio of the cross-sectional area to cross-sectional perimeter of a channel, one can judiciously vary the depth and width of a channel to affect the flow.

Input and output (entry and exit) ports are components of the microplatforms of the invention that are used for the introduction of removal of a variety of fluid components. Entry ports are provided to allow samples and reagents to be placed on or injected onto the disk; these types of ports are generally located towards the center of the disk. Exit ports are also provided to allow products to be removed from the disk. Port shape and design vary according specific applications. For example, sample input ports are designed, inter alia, to allow capillary action to efficiently draw the sample into the disk. In addition, ports can be configured to enable automated sample/reagent loading or product removal. Entry and exit ports are most advantageously provided in arrays, whereby multiples samples are applied to the disk or to effect product removal from the microplatform.

Also included in air handling systems on the disk are air displacement channels, whereby the movement of fluids displaces air through channels that connect to the fluid-containing microchannels retrograde to the direction of movement of the fluid, thereby providing a positive pressure to further motivate movement of the fluid.

Temperature control elements are provided to control the temperature of the platform during incubation of a fluid thereupon. The invention therefore provides heating elements, including heat lamps, direct laser heaters, Peltier heat pumps, resistive heaters, ultrasonication heaters and microwave excitation heaters, and cooling elements including Peltier devices and heat sinks, radiative heat fins and other components to facilitate radiative heat loss. Thermal devices are preferably arrayed to control the temperature of the platform over a specific area or multiplicity of areas. Preferably, heating and cooling elements comprise the platforms of the invention comprising a thermal regulation layer in the platform surface that is in thermal contact with the microfluidics components, most preferably microchannels as described herein. The temperature of any particular area on the platform (preferably, the microchannels at any particular thermally regulated area) is monitored by resistive temperature devices (RTD), thermistors, liquid crystal birefringence sensors or by infrared interrogation using IR-specific detectors, and can be regulated by feedback control systems. Temperature control on the microsystems platforms of this invention is most preferably achieved using the methods and devices disclosed in co-owned U.S. Pat. No. 6,063,589, incorporated by reference herein.

In preferred embodiments, portions of the microsystems platform surface are adapted for providing regions of controlled temperature (termed "thermal regions" or "thermal arrays" herein) using integral heating elements as disclosed in U.S. Pat. No. 6,063,589, incorporated by reference. In more preferred embodiments, the portions of the microsystems platform surface are constituted in arrays of thermal control elements, most preferably wherein is produced adjacent regions of the platform surface having different temperatures. In preferred embodiments, the platform also comprises other components as disclosed in co-owned and co-pending patent applications U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; 09/315,114, filed May 19, 1999, the disclosures of each of which are explicitly incorporated by reference herein, most preferably channels and microchannels, whereby fluid flow transverses each of the different regions having different temperatures at least once, or more preferably, several times. In these embodiments, the amount of time fluid is within any particular thermal region, and thus at any particular temperature is dependent on the path length of the channel in the region, the square of the hydraulic diameter of the channel, and the square of the rotational speed of the platform. In preferred embodiments, the arrays comprise at least 2 or 3 regions of different temperature adjacent to one another. In certain embodiments, the thermal regions are rectangular in shape, while in order embodiments the thermal regions are wedge-shaped, having a broader annular diameter at positions distal to the axis of rotation than at positions proximal to the axis of rotation.

In preferred embodiments of the platforms of the invention, the thermal arrays and regions of elevated temperatures constructed in the surface of the platforms of the invention comprise a thermal heating element. In preferred embodiments, the thermal heating element is a resistive heater element or a thermofoil heater, which is an etched-foil heating element enclosed in an electrically insulating plastic (Kapton, obtained from Minco). Resistive heater elements comprising the platforms of the invention are as described in co-owned U.S. Pat. No. 6,063,587. Briefly, said resistive heater elements comprise in combination an electrically inert substrate capable of being screen printed with a conductive ink and a resistive ink; a conductive ink screen-printed in a pattern; and a resistive ink screen-printed in a pattern over the conductive ink pattern wherein the resistive ink in electrical contact with the conductive ink and wherein an electrical potential applied across the conductive ink causes current to flow across the resistive ink wherein the resistive ink produces heat. Such structures are defined as "electrically-resistive patches" herein. Preferably, the conductive ink is a silver conductive ink such as Dupont 5028, Dupont 5025, Acheson 423SS, Acheson 426SS and Acheson SS24890, and the resistive ink is, for example, Dupont 7082, Dupont 7102, Dupont 7271, Dupont 7278 or Dupont 7285, or a PTC (positive temperature coefficient) ink. In alternative embodiments, the resistive heater element can further comprise a dielectric ink screen-printed over the resistive ink pattern and conductive ink pattern.

When the ratio between heater surface area and fluid volume is large, the time to heat the fluid to a desired temperature can be fast. The time for fluid to reach an equilibrium temperature can be approximated by the square of the channel depth divided by the thermal diffusivity of the fluid. For water, the thermal diffusivity is about $1.44 \times 10^{-4}$ $cm^2/sec$ and for a channel 50 µm deep (i.e., $5 \times 10^{-3}$ cm), the time required to reach thermal equilibrium is calculated to be about 0.2 sec. For amplification reactions like PCR, it is desirable to ensure that it takes a hypothetical liquid front much longer than the thermal equilibrium time to traverse a particular temperature region on the disc surface. For example, using a platform of the invention having microchannels with an interior dimension of 50 m, an overall channel length of 20 cm and a rotational speed of 590 rpm, when the mean distance of the fluid from the center of the disk is 3 cm and the radial extent of the fluid subject to centripetal force is 5 cm, the flow rate is about 6 mL/sec. Thus, for fluid volumes greater than 6 nL, the traversal time for any given temperature region on the disc is greater than 1 second. Since 1 sec >0.2 sec, there is sufficient time for the fluid to reach thermal equilibrium for each temperature region traversed for typical fluid volumes used on the disc.

Figure 2:
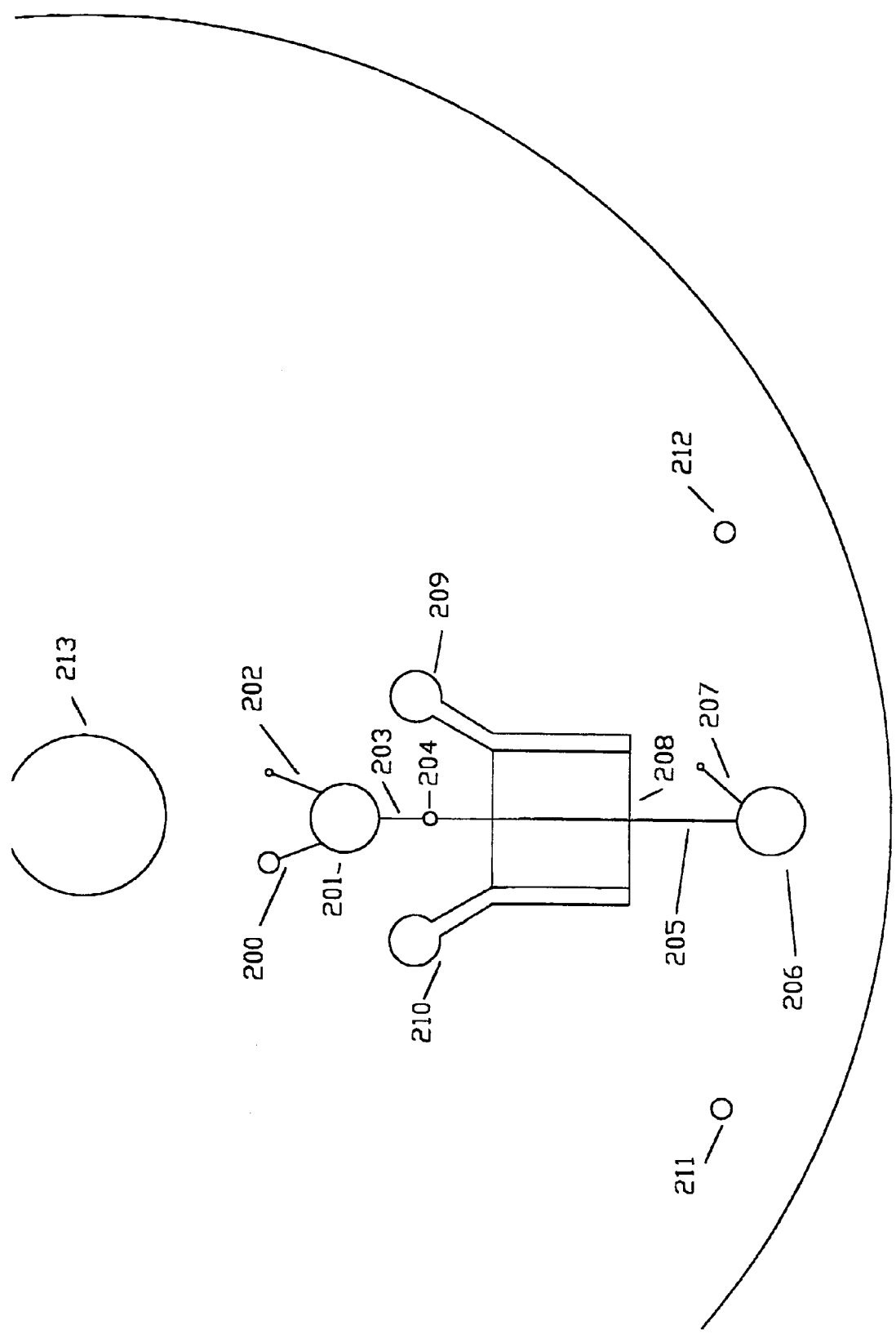
FIG. 2 depicts a plan view of the microsystems platform shown in oblique view in FIG. 1.
Figure 3:
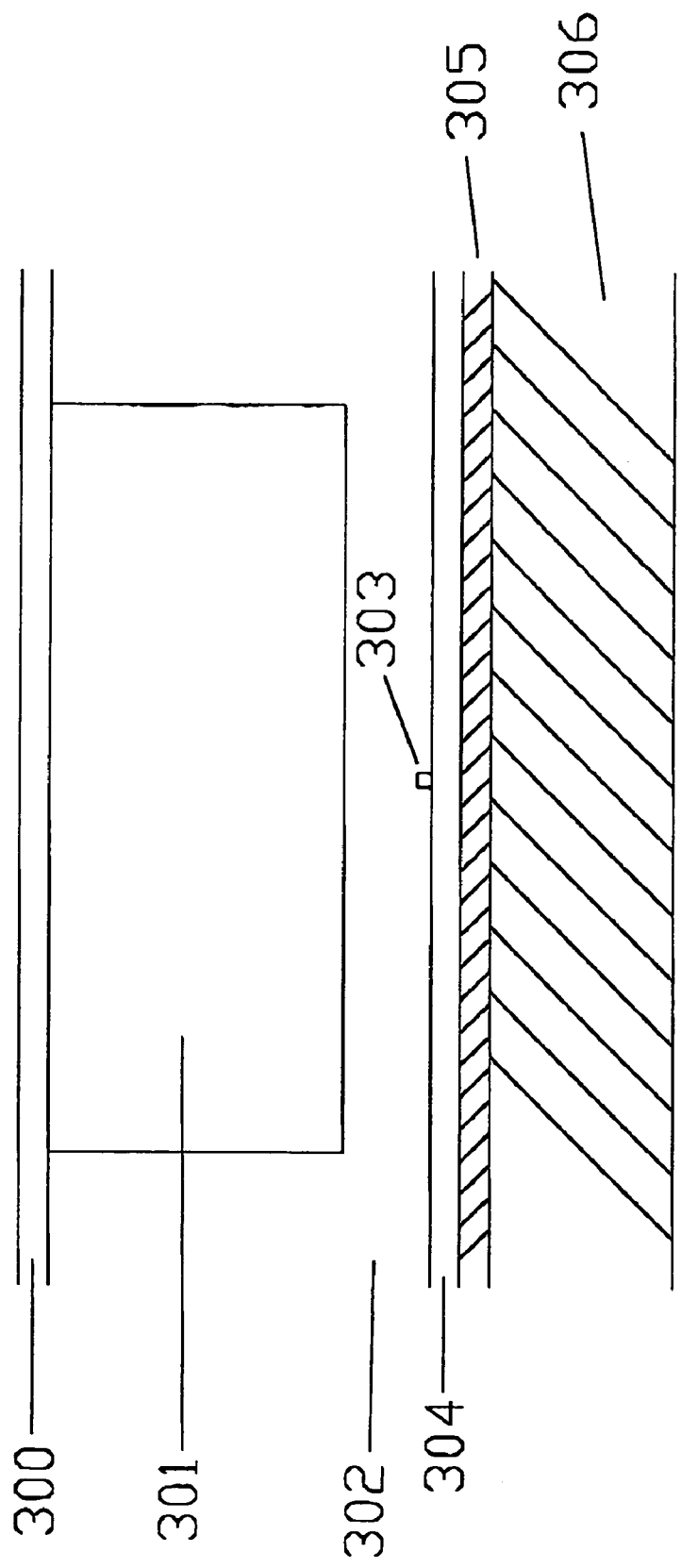
FIG. 3 is a cross-sectional view of the microsystems platform shown in FIGS. 1 and 2.

Referring now to the Figures for a more thorough description of the invention, FIG. 1 shows an oblique view, FIG. 2 shows a plan view and FIG. 3 shows a cross-sectional view of a platform of the invention. Fluidic manifold layer 100 comprises the microfluidic components of the platform including a fluid input port and input chamber 101, microchannel 102 and fluid collection chamber 103. Thermal regulation layer 113 comprises the heater elements of the platform, including a pair of electrically conductive leads 107 and 108 connected to electrically resistive patch 106. Fiducial marks 104, 105, 109 and 110 are use to align the manifold layer 100 and thermal regulation layer 113. When fiducial mark 104 is aligned with 109 and fiducial mark 105 is aligned with 110, the two layers are pressed together resulting in the plan view shown in FIG. 2. When so assembled, the layers rotate together about a spindle inserted in the inner hole 111.

In the plan view of this platform shown in FIG. 2 is depicted the assembled platform. Fluid input port 200 is fluidly connected to fluid holding chamber 201 having a volumetric capacity of from about 1 to about 200 µL. The fluid input port has a sufficient diameter to accommodate a standard 200 µL plastic pipette tip. The fluid holding chamber 201 has a diameter of from about 0.3 to about 1 cm and a depth in the platform surface of from about 0.02 to about 1 cm. Air displacement channel 202 having a cross-sectional dimension of from about 100 to about 500 µm is connected to fluid holding chamber 201 to permit displacement of air in fluid holding chamber 201 upon loading of a fluid sample into fluid input port 200. The fluid holding chamber is fluidly connected through microchannel 203 having a cross-sectional dimension of from about 1 to about 200 µm to microchannel 205. Microchannel 205 has a cross-sectional dimension of from about 1 to about 200 µm. A capillary microvalve 204 or, optionally, a sacrifical valve 204, interrupts microchannel 203 and prevents fluid flow from fluid holding chamber 201 into microchannel 205 in the absence of platform rotation (i.e., at zero centripetal force). Microchannel 205 is fluidly connected to collection chamber 206 having volumetric capacity of from about 1 to about 200 µL. Collection chamber 206 has a diameter of from about 0.3 to about 1 cm and a depth in the platform surface of from about 0.02 to about 1 cm. Air displacement channel 207 having a cross-sectional dimension of from about 100 to about 500 µm is connected to collection chamber 206 to permit displacement of air in collection chamber 206 upon rotation of the platform and fluid flow from fluid holding chamber 201 through microchannel 205 and into collection chamber 206.

Thermal control of the fluid flowing through microchannel 205 is accomplished by heating the fluid and microchannel using electrically-resistive patch 208. Electrically conductive leads 209 and 210 control heating by electrically-resistive patch 208. The time during which the fluid in microchannel 205 is maintained at a temperature greater than ambient is dependent on the rotational speed of the platform and the length and interior dimension of microchannel 205.

The cross-sectional view of the platform is shown in FIG. 3. Electrically-resistive patch 305 is on the surface of thermal regulation layer substrate 306, and fluidic manifold layer 302 containing microfluidic structures including microchannel 303 in substrate layer 304 are pressed together in place using fiducial registers as shown in FIGS. 1 and 2. An insulation space 301 having a volumetric capacity of from about 0.1 to about 1 cm$^3$ is advantageously positioned in manifold layer 302 above the position of electrically-resistive patch 305 in thermal regulation layer 306. This insulation space is optionally enclosed by cover 300. Insulation space 301 can be empty (i.e., containing only air) or can contain air trapped in fibrous material. Insulation space 301 supports the formation of a temperature gradient between the heater and the environment and permits the formation of a uniform temperature through the thickness of the capillary microchannel.

The platform shown in FIGS. 1-3 is useful for binding assays at a controlled temperature greater than the ambient temperature of the platform. For example, hybridization probes deposited on the walls of the microchannel, or comprising carrier beads that are motivated into the capillary channel can be used to separate hybridizing from non-hybridizing material in a biological sample, particularly if the carrier beads are retained in the microchannel.

Figure 4:
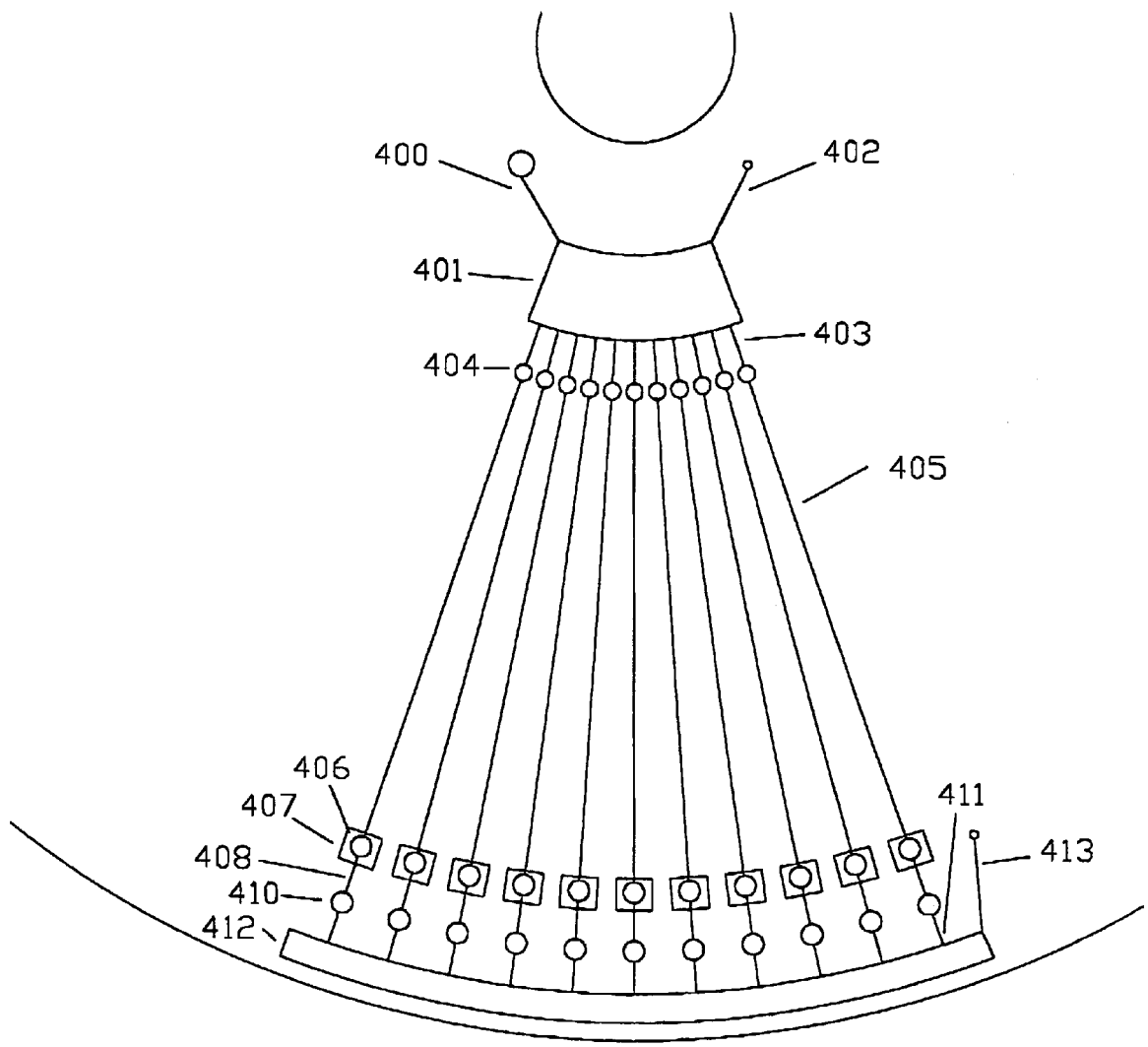
FIG. 4 shows a plan view of a microsystems platform comprising a multiplicity of fluidic and thermal regulatory structures for performing a nucleic acid hybridization reaction.

FIG. 4 shows a microsystems platform according to the invention adapted for performing hybridization arrays. In the Figure, fluid input port 400 is fluidly connected to fluid holding chamber 401 having a volumetric capacity of from about 10 to about 200 µL. The fluid input port has a sufficient diameter to accommodate a standard 200 µL plastic pipette tip. Fluid holding chamber 401 has a diameter of from about 1 to about 3 cm and a depth in the platform surface of from about 0.02 to about 1 cm. Air displacement channel 402 having a cross-sectional dimension of from about 100 to about 500 µm is connected to fluid holding chamber 401 to permit displacement of air in fluid holding chamber 401 upon loading of a fluid sample into fluid input port 400. The fluid holding chamber is fluidly connected through a multiplicity of microchannels 403 having a cross-sectional dimension of from about 1 to about 200 µm to an equivalent multiplicity of microchannels 405. Microchannels 405 each have a cross-sectional dimension of from about 1 to about 200 µm. Capillary microvalves 404 or, optionally, sacrificial valves 404, interrupt microchannels 403 and prevent fluid flow from fluid holding chamber 401 into microchannels 405 in the absence of platform rotation (i.e., at zero centripetal force). Microchannels 405 are fluidly connected to hybridization chambers 406 having volumetric capacity of from about 1 to about 20 µL. The hybridization chambers have a diameter of from about 0.1 to about 1 cm and a depth in the platform surface of from about 10 to about 200 µm. Positioned in thermal contact with each of hybridization chambers 406 are heating elements 407, most preferably electrically-resistive patches contained in a thermal regulation layer as shown in FIGS. 1-3. Hybridization chambers 406 are optionally and advantageously fluidly connected to detection chambers 410. Detection chambers 410 enable detection of hybridization reaction products, most preferably using optical detectors and detection methods, as described more completely in 6,063,589, issued May 16, 2000, and co-owned and co-pending patent applications U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; and 09/315,114, filed May 19, 1999, the disclosures of each of which are explicitly incorporated by reference herein.

Detection chambers 410 are fluidly connected through capillaries 411 having an interior dimension of from about 1 to about 200 µm to common waste chamber 412, that has a diameter of from about 1 to about 3 cm and a depth in the platform surface of from about 0.02 to about 0.2 cm. Air displacement channel 413 having a cross-sectional dimension of from about 100 to about 500 µm is connected to common waste chamber 412 to permit displacement of air in common waste chamber 412 upon rotation of the platform. Uses of this type of platform are exemplified herein in Example 1.

Figure 5:
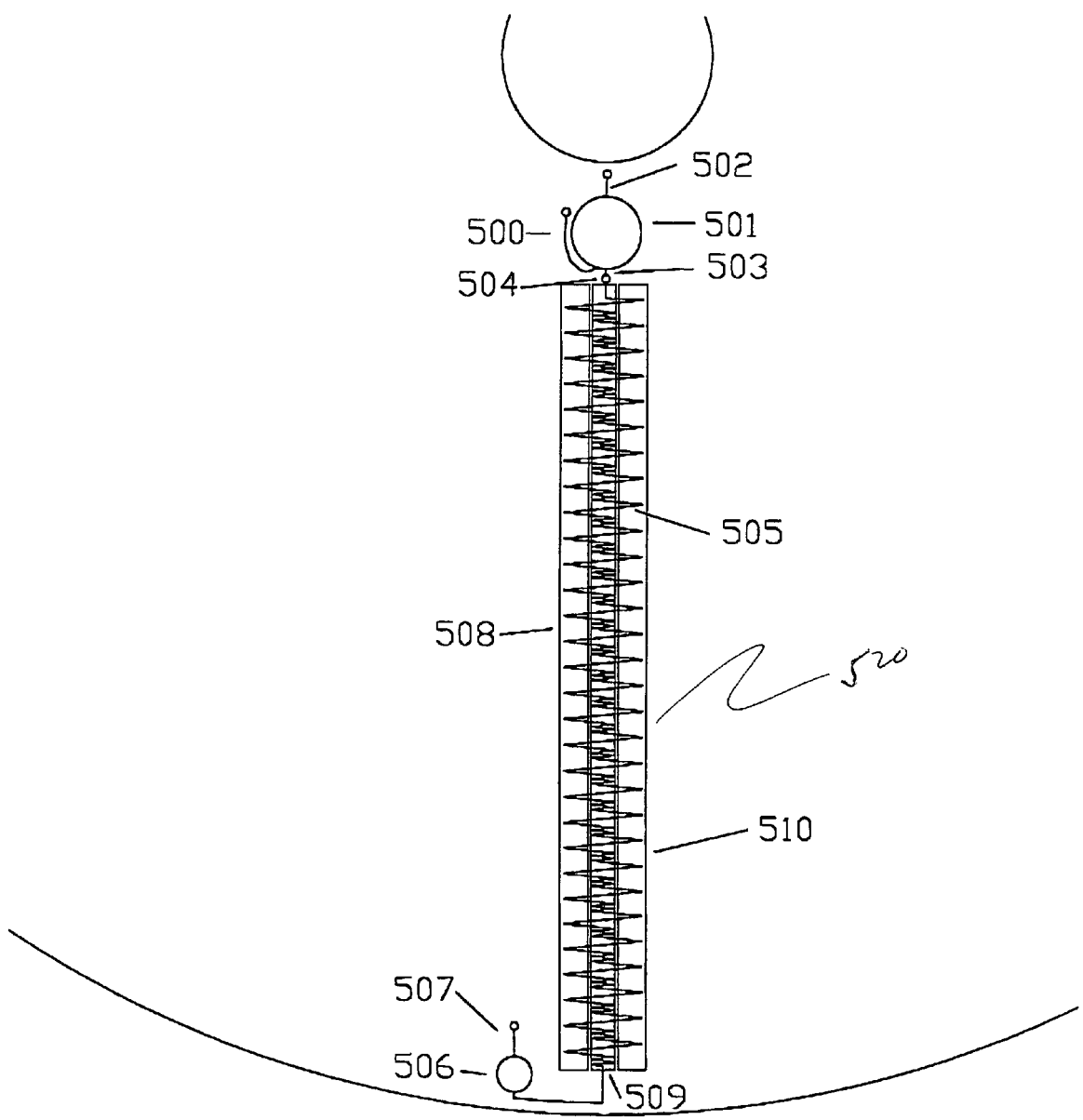
FIG. 5 shows a plan view of a microsystems platform adapted for performing an in vitro amplification reaction.
Figure 6:
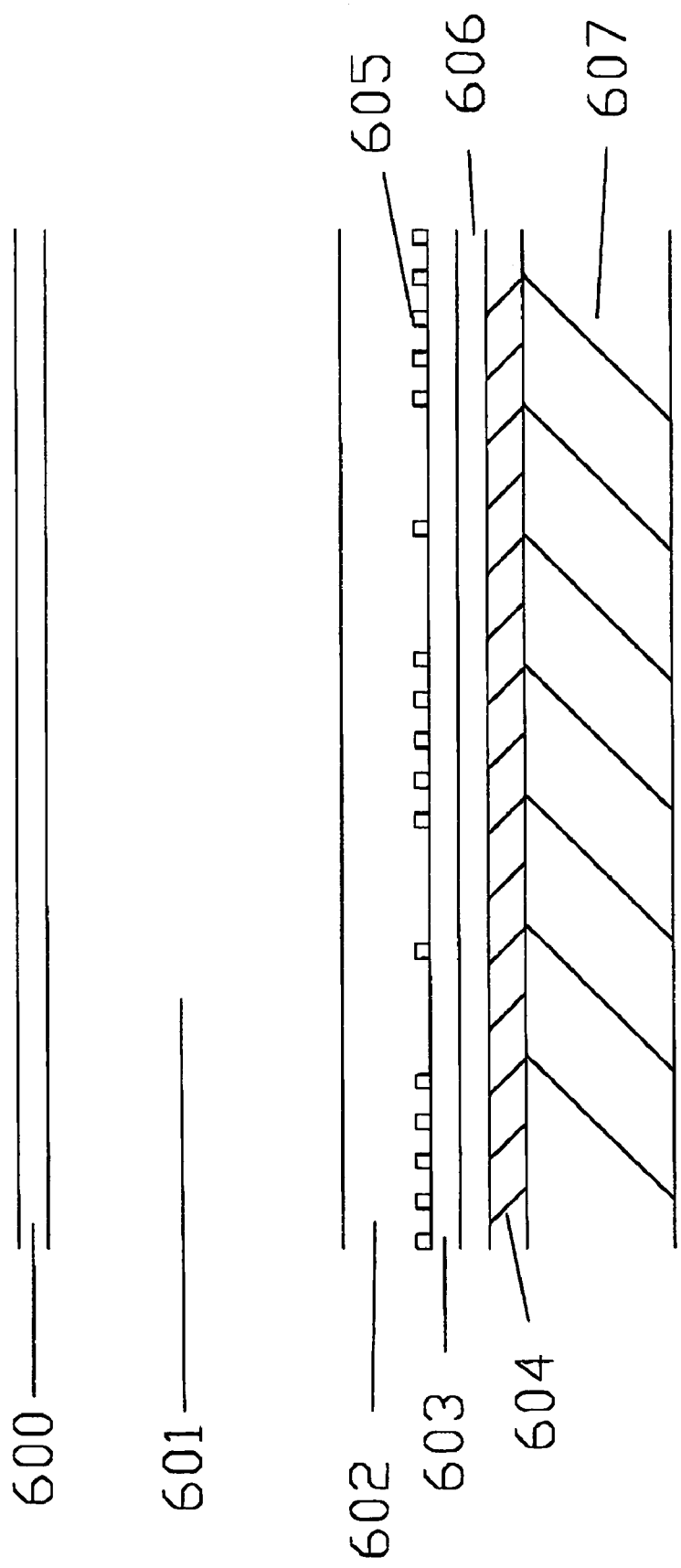
FIG. 6 is a cross-sectional view of the platform shown in FIG. 5.

FIGS. 5 and 6 depict plan and cross-sectional views of a microfluidics platform of the invention adapted for performing polymerase chain reaction or ligase chain reaction. In FIG. 5, a fluid input port 500 is fluidly connected to fluid holding chamber 501 having a volumetric capacity of from about 10 to about 200 µL. The fluid input port has a sufficient diameter to accommodate a standard 200 µL plastic pipette tip. Fluid holding chamber 501 has a diameter of from about 1 to about 3 cm and a depth in the platform surface of from about 0.02 to about 0.3 cm. Air displacement channel 502 having a cross-sectional dimension of from about 100 to about 500 µm is connected to fluid holding chamber 501 to permit displacement of air in fluid holding chamber 501 upon loading of a fluid sample into fluid input port 500. The fluid holding chamber is fluidly connected through microchannel 503 having a cross-sectional dimension of from about 1 to about 200 µm to thermal array 520. A capillary microvalve 504 or, optionally, a sacrifical valve 504, interrupts microchannel 503 and prevents fluid flow from fluid holding chamber 501 into thermal array 520 in the absence of platform rotation (at zero centripetal force).

Thermal array 520 comprises a fluid microchannel 505 that traverses the array across three thermal zones comprising individually-addressable heating elements 508, 509 and 510, preferably comprising a thermal regulation layer as described above and in FIG. 6. Fluid microchannel 505 has a cross-sectional dimension of from about 1 to about 200 µm. The path of microchannel 505 is shown in the Figure to represent different transit times across the different thermal zones. As shown in the Figure, the transit time in the middle thermal zone is longer than in either of the flanking thermal zones, because the microchannel path traverses this zone several times for each time the path traverses either of the flanking zones. Microchannel paths traversing the thermal zones having equal transit times or any combination of differential transit times for each zone are within the scope of this invention. Heating elements 508, 509 and 510 are constructed to be operated at separate and distinct temperatures greater than ambient; such heating elements are described more fully in co-owned U.S. Pat. No. 6,063,589 issued May 16, 2000 and in co-owned and co-pending patent applications U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; 09/315,114, filed May 19, 1999, incorporated by reference. The width and length of the heating elements comprising thermal zones depicted in FIG. 5 will depend on the incubation time desired for the fluid to be at each of the different temperatures in the different thermal zones. Typically, the length of the microchannel is chosen to be equivalent to 20-35 cycles of conventional PCR, wherein each cycle consists of a time interval at a denaturing temperature (from about 80° C. to about 95° C.), a time interval at an oligonucleotide primer annealing temperature (from about 40° C. to about 65° C.) and a time interval at a polymerase extension temperature (from about 60° C. to about 75° C.).

In alternative embodiments, the middle thermal zone is provided without a heating element, so that transit through this zone is at ambient temperature. It will be recognized that other configurations of the thermal arrays of the invention, as described herein, are also useful in constructing alternative platforms of the invention based on the platform explicitly disclosed in FIG. 5.

Figure 7:
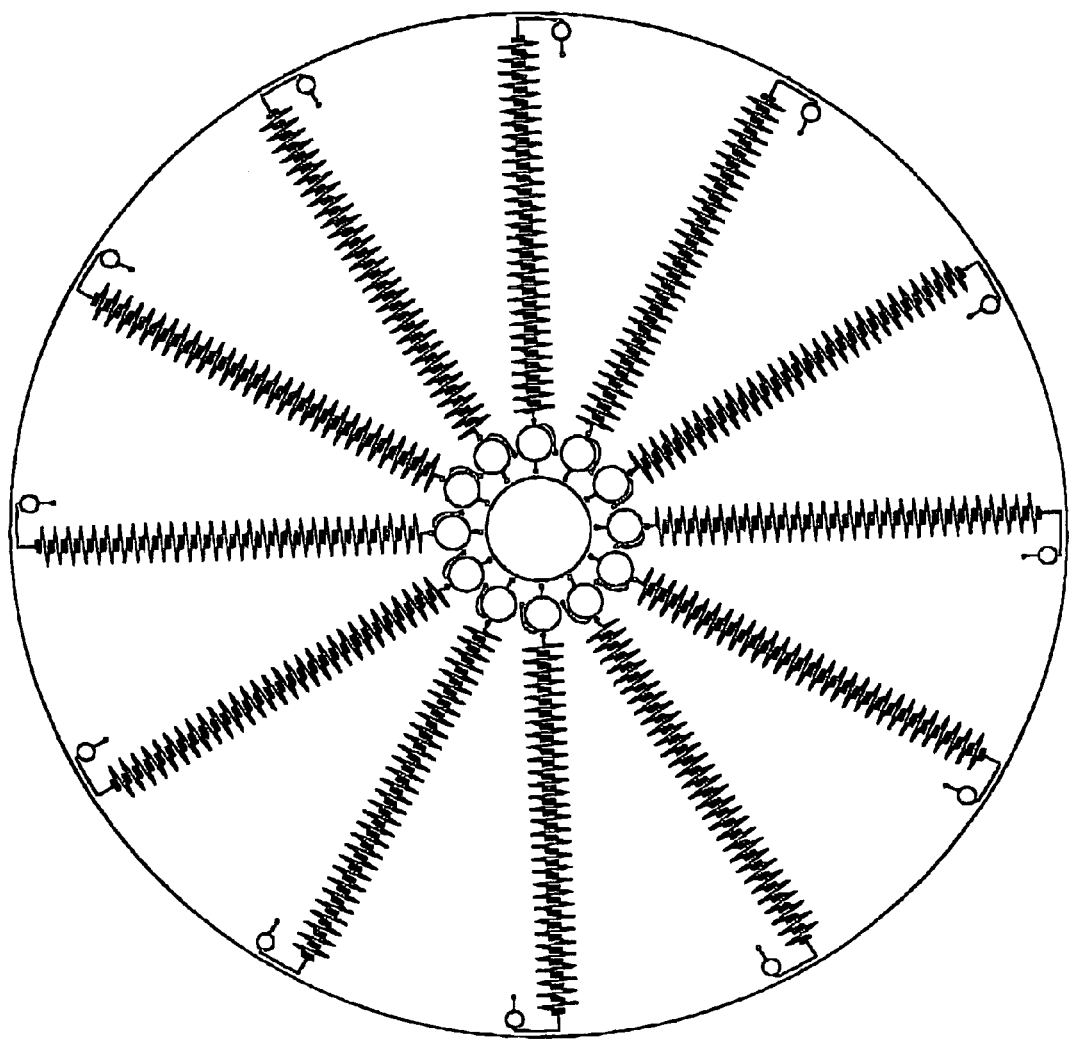
FIG. 7 shows the arrangement of twelve fluidic structures as depicted in FIG. 5 around the interior diameter of a disc.

It will also be recognized that platforms comprising a multiplicity of the microfluidic and thermal structures shown in FIG. 5 are also encompassed by the invention, wherein individual fluid input and holding chambers, or such chambers shared in common, are provided fluidly connected to the thermal arrays of the invention. An example of such a platform is shown in FIG. 7.

FIG. 6 shows a cross-sectional view of the platform of FIG. 5. Heating element 604 is shown on the surface of thermal regulation layer substrate 607, and fluidic manifold layer 602 containing microfluidic structures including microchannels 605 in substrate layer 603 are pressed together in place using fiducial registers as shown in FIGS. 1 and 2. Thermal conductive layer 606 is optionally included between the fluidic manifold layer and the thermal regulation layer to increase thermal conductivity and heat transfer to the fluid in microchannels 605. An insulation space 601 having a volumetric capacity of from about 0.3 to about 3 cm$^3$ is advantageously positioned in fluidic manifold layer 602 above the position of the heating element 604 in thermal regulation layer 607. This insulation space is optionally enclosed by cover 600.

In some embodiments of the invention, the platform comprises a single thermal array. It will be recognized by those will skill in the art that such embodiments are useful for multiplex assay of a single sample or assays of multiple samples. Platforms of the invention are provided having, for example, multiple embodiments of the thermal arrays as described herein, in fluid communication with one or a multiplicity of sample entry ports. Thus, in more preferred embodiments, the platforms of the invention comprise a multiplicity of such arrays laid out on the platform surface as exemplified in FIG. 7.

In alternative embodiments, the fluidic manifold layer and thermal regulation layer are integrally micromachined onto a single substrate layer. In additional alternative embodiments, the thermal regulation layer comprises a platen that is in the thermal contact with a fluidic microsystems platform of the invention, wherein the fluidic components such as microchannels are positioned to be in thermal contact with heating elements on the platen, most preferably using fiducials or other mechanical components that orient the platform and platen with one another.

In alternative embodiments, the thermal regulating layer is a mechanical platen, in which the microfluidic components are positioned in thermal contact with heating elements on the platen. A platen as the term is used herein is in certain embodiments a circuit board having electrical components mounted and soldered thereupon. In its simplest form, the electrical components are passive and consist primarily of resistors in defined locations on the platen. Heat is produced using such resistors because power is dissipated as heat when a voltage is applied across a resistor. The heat dissipation is proportional to the square of the applied voltage divided by the resistance of the resistor.

In certain embodiments, the platen comprises a multiplicity of resistors that share a common ground but that have different input wires so that different voltages can be applied and different temperatures obtained in microfluidics components placed proximate to each of the resistors. Typically, the electrical signal is distributed from the micromanipulation device to the platen through a slip-ring assembly, as described more fully in co-owned U.S. Pat. No. 6,063,589, incorporated by reference. However, as the multiplicity of resistors increases, the required number of slips can be impractical. For these embodiments, platens comprising integrated circuits, microprocessors and other "active" components are advantageously utilized.

The following Examples are intended to further illustrate certain preferred embodiments of the invention and are not limited in nature.

EXAMPLE 1

Microplatform Disk for DNA Hybridization

A series of hybridization reactions performed to determine the optimum hybridization stringency conditions between a probe molecule and a specific gene sequence is performed using the microsystems platform shown in FIG. 4. A denatured hybridization mixture comprising the probe, the specific gene sequence, salts, buffers, detergents and hybridization facilitating agents such as dimethylformamide is applied to fluid holding chamber 401 at rest. The platform is then rotated at a first rotation speed sufficient to overcome capillary microvalve 404 and the hybridization solution traverses microchannels 405 and is deposited in substantially equal volumes into hybridization chambers 406. Heating elements 407 are independently operated at a series of incrementally different and increasing temperatures, so that hybridization is achieved over a range of temperatures from ambient to a temperature at which no hybridization occurs. After the hybridization mixture is incubated in hybridization chambers 406 for a time sufficient for hybridization to have proceeded to completion under the temperature conditions in each chamber, the platform is rotated at a second rotation speed higher than the first rotation speed, and the hybridization reaction mixtures from each hybridization chamber are transferred to detection chambers 410. The extent of hybridization is analyzed in each detection chamber using conventional methods, for example, absorbance at 260 nm; in this embodiment, the portion of the platform comprising detection chambers 410 is transparent to ultraviolet light. The temperature conditions yielding the greatest extent of hybridization are determined thereby.

EXAMPLE 2

Microplatform Disk for DNA Amplification

An amplification reaction is performed on the microsystems platform disclosed in FIGS. 5 and 6 as follows. While the disk is stationary, 10 µL of a fluid reaction mixture containing template DNA, PCR amplification primers, deoxynucleotide triphosphates, and thermostable polymerase in a buffer solution in which the reaction may proceed are applied to fluid input port 500. As the fluid fills fluid holding chamber 501 air is displaced through air displacement channels 502 and 507; in this example, 501 has a diameter of 0.4 cm and a depth of 0.3 cm and 10 µL fills approximately 25% of the volumetric capacity of fluid holding chamber 501. Fluid also flows into microchannel 503 until it reaches the capillary microvalve 504 or optional sacrifical valve 504. Once loaded, the platform is briefly rotated at about 3000 rpm to overcome the capillary microvalve, or optionally the sacrificial valve is opened, and then the rotational speed is lowered to about 590 rpm. At this rotational speed, fluid flows through fluid microchannel 505 at a rate of about 6 nL/sec, as the microchannel has a hydraulic diameter of 50 µm and a overall length of approximately 20 cm. At this rate, it takes approximately 30 min for the 10 µL reaction mixture to traverse the thermal array 520 and be deposited in collection chamber 506. As shown in FIG. 5, traversal of the thermal array subjects the fluid to 30 cycles of alternative temperatures, equivalent to 30 cycles of PCR as conventionally performed.

It should be understood that the foregoing disclosure emphasizes certain specific embodiments of the invention and that all modifications or alternatives equivalent thereto rate within the spirit and scope of the invention.

What is claimed is:

1. A centripetally-motivated microsystems platform comprising:
    a) a rotatable platform comprising a substrate having a surface comprising one or a multiplicity of microchannels embedded therein and defining a longitudinal path across the surface of the platform;
    b) a sample input port comprising a depression in the surface having a volumetric capacity of about 1 to about 200/µL;
    c) a collection chamber comprising a depression in the surface having a volumetric capacity of about 1 to about 200/µL;
    wherein the sample input port and collection chamber are fluidly connected to the microchannels;
    d) one or a multiplicity of heating elements comprising at least one region of the platform surface;
    wherein at least a portion of the longitudinal path of the microchannels is in thermal contact with the one or multiplicity of heating elements;
    wherein a volume of a fluid within the microchannels of the rotatable platform is moved through said microchannels by centripetal force arising from rotational motion of the rotatable platform for a time and a rotational velocity sufficient to move the fluid through the microchannels, and
    wherein fluid in the microchannels is heated with the one or a multiplicity of heating elements to a temperature greater than the ambient temperature of the platform as said fluid moves through the portion of the microchannels in thermal contact with the heating element.

2. A microsystem platform of claim 1 having one sample input port and a multiplicity of microchannels, wherein the sample input port is fluidly connected to each of the microchannels.

3. A microsystem platform of claim 1 having a multiplicity of sample input ports and a multiplicity of microchannels, wherein each microchannel is fluidly connected to a sample input port.

4. A microsystem platform of claim 1 having one collection chamber and a multiplicity of microchannels, wherein the collection chamber is fluidly connected to each of the microchannels.

5. A microsystem platform of claim 1 having a multiplicity of collection chambers and a multiplicity of microchannels, wherein each microchannel is fluidly connected to a collection chamber.

6. A microsystems platform of claim 1 wherein the heating element comprises a rectangular portion of the surface of the platform.

7. A microsystem platform of claim 1 wherein the heating element comprises a wedge-shaped portion of the surface of the platform.

8. A microsystem platform of claim 7, wherein the wedge-shaped portion is arrayed on the platform so that the longer annular diameter is farther from the center of the platform than the shorter annular diameter.

9. A microsystem platform of claim 1 that is a circular disk.

10. The microsystem platform of claim 9, wherein the microsystem platform is a circular disk having a radius of about 1 to about 25 cm.

11. The microsystem platform of claim 1, wherein the microsystem platform is constructed of a material selected from the group consisting of an organic material, an inorganic material, a crystalline material and an amorphous material.

12. The microsystem platform of claim 11, wherein the microsystem platform further comprises a material selected from the group consisting of silicon, silica, quartz, a ceramic, a metal or a plastic.

13. The microsystem platform of claim 1, wherein the microsystem platform has a thickness of about 0.1 to 100 mm, and wherein the cross-sectional dimension of the microchannels embedded therein is less than 500 gm and from 1 to 90 percent of said cross-sectional dimension of the platform.

14. The microsystem platform of claim 1, wherein the microsystem platform further comprises a multiplicity of air channels, exhaust air ports and air displacement channels.

15. The microsystems platform of claim 1 wherein the microchannels are arrayed linearly from the center of the platform to the periphery.

16. The microsystems platform of claim 1 wherein the microchannels are arrayed concentrically from the center of the platform to the periphery.

17. The microsystem platform of claim 1, wherein the heating element comprises a resistive heater element.

18. A microsystem platform according to claim 1 comprising a multiplicity of heating elements.

19. A microsystem platform according to claim 18 wherein the multiplicity of heating elements comprises a pair of heating elements placed adjacent to on another on the surface of the platform.

20. A microsystem platform according to claim 19, wherein the adjacent heating elements are immediately adjacent to one another.

21. A microsystems platform according to claim 19, wherein the adjacent heating elements are separated by an unheated portion of the platform that is no wider than the width of one of the adjacent heating elements.

22. A microsystems platform according to claim 19, 20 or 21, wherein a portion of the longitudinal path of the microchannels is contained within the region of the platform surface comprising each of the heating elements.

23. A microsystem platform according to claim 19, wherein the platform comprises a multiplicity of adjacent pairs of heating elements separated by a portion of the platform.

24. A microsystem platform according to claim 19, wherein the platform comprises a multiplicity of adjacent three heating elements separated by an unheated portion of the platform.

25. A microsystem platform according to claim 22, wherein each of the heating elements is operated at a temperature greater than ambient temperature of the platform.

26. A microsystems platform of claim 25, wherein each of the heating elements is operated at a temperature different from the other heating element and greater than the ambient temperature of the platform.

27. A microsystems platform of claim 25 or 26 wherein one of the heating elements is operated at a temperature of from about 80° C. to about 98° C. and the other heating element is operated at a temperature of about 65° C. to about 75° C.

28. A microsystem platform according to claim 18 wherein the multiplicity of heating elements comprises three heating elements placed adjacent to one another on the surface of the platform.

29. A microsystem platform according to claim 28, wherein the adjacent heating elements are immediately adjacent to one another.

30. A microsystems platform according to claim 28, wherein one or both of the adjacent heating elements are separated by an unheated portion of the platform that is no wider than the width of one of the adjacent heating elements.

31. A microsystems platform according to claim 28, 29 or 30, wherein a portion of the longitudinal path of the microchannels is contained within the region of the platform surface comprising each of the heating elements.

32. A microsystems platform according to claim 31, wherein each of the heating elements is operated at a temperature greater than ambient temperature of the platform.

33. A microsystems platform of claim 32, wherein each of the heating elements is operated at a temperature different from the other heating element and greater than the ambient temperature of the platform.

34. A microsystems platform of claim 32 or 33 wherein one of the heating elements is operated at a temperature of from about 80° C. to about 98° C. one of the heating elements is operated at a temperature of about 40° C. to about 65° C., and the other heating element is operated at a temperature of about 60° C. to about 75° C.

35. A microsystems platform according to claim 34, wherein the heating element operated at a temperature of from about 60° C. to about 75° C. is positioned in between the other two heating elements.

36. A microsystems platform according to claim 35, wherein the portion of the longitudinal extent of the microchannels is greater in the region of the platform surface comprising the heating element operated at a temperature of from about 60° C. to about 75° C. than the portion of the microchannels in the regions comprising either of the other two heating elements.

37. A microsystem platform according to claim 18, wherein the multiplicity of heating elements comprise a thermal array.

38. A microsystem platform according to claim 31, wherein the thermal array comprises a single heating element.

39. A microsystem platform according to claim 38, wherein the thermal array comprises a multiplicity of heating elements.

40. A centripetally-motivated fluid micromanipulation apparatus that is a combination of
 a microsystem platform according to claim 1, and
 a micromanipulation device, comprising a base, a rotating means, a power supply and user interface and operations controlling means, wherein the rotating means is operatively linked to the microsystem platform and in rotational contact therewith
 wherein a volume of a fluid within the microchannels of the platform is moved through said microchannels by centripetal force arising from rotational motion of the platform for a time and a rotational velocity sufficient to move the fluid through the microchannels.

41. The apparatus of claim 40, wherein the rotating means of the device is an electric motor.

42. The apparatus of claim 40, wherein the device comprises a rotational motion controlling means for controlling the rotational acceleration and velocity of the microsystem platform.

43. A microsystem platform of claim 1, wherein the microchannels, sample input port and collection chamber are contained in the surface of the platform, and the heating elements comprise a platen in thermal contact with the microsystems platform.

44. A microsystems platform according to claim 1, wherein the portion of the longitudinal extent of the microchannels are linear, curved, spiral, zig-zag or meandering.

45. A microsystems platform according to claim 1, wherein the surface of the platform comprising the collection chamber is optically transparent.

46. A microsystems platform of claim 1, wherein the multiplicity of heating elements can be operated at different temperatures.

47. A microsystems platform of claim 46, wherein the proportion of time the fluid is maintained at a particular temperature is directly proportional to the longitudinal extent of the microchannel in the region.

48. The microsystems platform of claim 46, wherein the microchannels are arranged such that fluid traveling through the microchannels can repeatedly leave any particular temperature region on the disk.

* * * * *